(12) United States Patent
Bilsborough et al.

(10) Patent No.: US 7,041,502 B2
(45) Date of Patent: May 9, 2006

(54) ISOLATED PEPTIDES WHICH BIND TO HLA-B18 MOLECULES AND USES THEREOF

(75) Inventors: Janine Bilsborough, Seattle, WA (US); Erwin Schultz, Erlagen (DE); Christophe Panichelli, Brussels (BE); Thierry Boon, Brussels (BE); Pierre Van der Bruggen, Brussels (BE)

(73) Assignee: Ludwig Institute for Cancer Research, New York, NY (US)

( * ) Notice: Subject to any disclaimer, the term of this patent is extended or adjusted under 35 U.S.C. 154(b) by 437 days.

(21) Appl. No.: 10/164,078

(22) Filed: Jun. 5, 2002

(65) Prior Publication Data

US 2003/0228325 A1    Dec. 11, 2003

(51) Int. Cl.
  *C12N 5/22*   (2006.01)
  *G01N 33/53*  (2006.01)
  *A61K 38/00*  (2006.01)
  *C07H 21/00*  (2006.01)

(52) U.S. Cl. .................. 435/372.3; 435/7.24; 530/324; 530/325; 530/326; 530/327; 530/328; 536/23.5

(58) Field of Classification Search ............ 424/277.1, 424/93.71; 514/15; 530/324–328, 388.8, 530/389.7; 435/7.23, 372.3, 7.24; 536/23.5
See application file for complete search history.

(56) References Cited

U.S. PATENT DOCUMENTS

| | | | |
|---|---|---|---|
| 5,750,395 A | | 5/1998 | Fikes et al. |
| 6,291,430 B1 * | | 9/2001 | Chaux et al. .................. 514/13 |
| 6,303,756 B1 | | 10/2001 | Martelange et al. |
| 2003/0228325 A1 | | 12/2003 | Bilsborough et al. |

OTHER PUBLICATIONS

Herman, J et al. Immunogenetics [1996] 43:377-383.*
Billsborough, J et al. Tissue Antigens [2002] 60:16-24.*
Berzofsky, JA. ASM News [2004] 70(5):219-223.*
Kirkin, AF et al. APMIS [1998] 106:665-679.*

* cited by examiner

*Primary Examiner*—Christina Chan
*Assistant Examiner*—F. Pierre VanderVegt
(74) *Attorney, Agent, or Firm*—Fulbright & Jaworski LLP

(57) ABSTRACT

A peptide, previously identified as a binding partner of HLA-B44, has now been found to bind to HLA-B18 forming a T cell epitope. The therapeutic and diagnostic ramifications of this are the subject of this invention, as are various products obtained in the course of the development of the invention.

11 Claims, No Drawings

US 7,041,502 B2

ISOLATED PEPTIDES WHICH BIND TO HLA-B18 MOLECULES AND USES THEREOF

FIELD OF THE INVENTION

This invention relates to peptides which form immunologically active complexes with MHC molecules. More particularly, it involves peptides based upon amino acid sequences found in the molecule referred to as "MAGE-3," which form complexes with the MHC molecule HLA-B18.

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T cells in the recipient animal, and provoke a cytolytic T cell response with lysis of the transplanted cells. This evidence was first obtained with tumors induced in vitro by chemical carcinogens, such as methylcholanthrene. The antigens expressed by the tumors and which elicited the T cell response were found to be different for each tumor. See Prehn, et al., J. Natl. Canc. Inst. 18: 769–778 (1957); Klein, et al., Cancer Res. 20:1561–1572 (1960); Gross, Cancer Res. 3:326–333 (1943), Basombrio, Cancer Res. 30:2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53:333–1336 (1974).

While T cell mediated immune responses were observed for the types of tumor described supra, spontaneous tumors were thought to be generally non-immunogenic. These were therefore believed not to present antigens which provoked a response to the tumor carrying subject. See Hewitt, et al., Brit. J. Cancer 33:241–259 (1976).

The family of tum⁻ antigen presenting cell lines are immunogenic variants obtained by mutagenesis of mouse tumor cells or cell lines, as described by Boon, et al., J. Exp. Med. 152:1184–1193 (1980), the disclosure of which is incorporated by reference. To elaborate, tum⁻ antigens are obtained by mutating tumor cells which do not generate an immune response in syngeneic mice and will form tumors (i.e., "tum⁺" cells). When these tum⁺ cells are mutagenized, they are rejected by syngeneic mice, and fail to form tumors (thus "tum⁻"). See Boon, et al., Proc. Natl. Acad. Sci USA 74:272 (1977), the disclosure of which is incorporated by reference. Many tumor types have been shown to exhibit this phenomenon. See, e.g., Frost, et al., Cancer Res. 43:125 (1983).

It appears that tum⁻ variants fail to form progressive tumors because they elicit an immune rejection process. The evidence in favor of this hypothesis includes the ability of "tum⁻" variants of tumors, i.e., those which do not normally form tumors, to do so in mice with immune systems suppressed by sublethal irradiation, Van Pel, et al. Proc. Natl, Acad. Sci. USA 76:5282–5285 (1979); and the observation that intraperitoneally injected tum⁻ cells of mastocytoma P815 multiply exponentially for 12–15 days, and then are eliminated in only a few days in the midst of an influx of lymphocytes and macrophages (Uyttenhove, et al., J. Exp. Med. 152:1175–1183 (1980)). Further evidence includes the observation that mice acquire an immune memory which permits them to resist subsequent challenge to the same tum⁻ variant, even when immunosuppressive amounts of radiation are administered with the following challenge to the same tum⁻ variant, even when immunosuppressive amounts of radiation are administered wit the following challenge of cells (Boon, et al., Proc. Natl, Acad. Sci. USA 74:272–275 (1977); Van Pel, et al., supra; Uyttenhove, et al., supra). Later research found that when spontaneous tumors were subjected to mutagenesis, immunogenic variants were produced which did generate a response. Indeed, these variants were able to elicit an immune protective response against the original tumor. See Van Pel, et al., J. Exp. Med. 157: 1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearon, et al., Cancer Res. 48:2975–1980 (1988) in this regard.

A class of antigens has been recognized which are presented on the surface of tumor cells and are recognized by cytotoxic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies, in vitro i.e., the study of the identification of the antigen by a particular cytolytic T cell ("CTL" hereafter) subset. The subset proliferates upon recognition of the presented tumor rejection antigen, and the cells presenting the antigen are lysed. Characterization studies have identified CTL clones which specifically lyse cells expressing the antigens. Examples of this work may be found in Levy et al., Adv. Cancer Res. 24:1–59 (1977); Boon, et al., J. Exp. Med. 152:1184–1193 (1980); Brunner, et al., J. Immunol. 124:1627–1634 (1980); Maryanski, et al., Eur. J. Immunol. 124:1627–1634 (1980); Maryanski, et al., Eur. J. Immunol. 12:406–412 (1982); Palladino, et al., Canc. Res. 47:5074–5079 (1987). This type of analysis is required for other types of antigens recognized by CTLs, including minor histocompatibility antigens, the male specific H-Y antigens, and a class of antigens, referred to as "tum⁻" antigens, and discussed herein.

A tumor exemplary of the subject matter described supra is known as P815. See DePlaen, et al, Proc. Natl. Acad. Sci. USA 85:2274–2278 (1988); Sikora, et al., EMBO J 9:1041–1050 (1990), and Sibille, et al., J. Exp. Med. 172: 35–45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum⁻ variants following mutagenesis, including variants referred to as P91A (DePlaen, supra), 35B (Szikora, supra) and P198 (Sibille, supra). In contrast to tumor rejection antigens—and this is a key distinction—the tum⁻ antigens are only present after the tumor cells are mutagenized. Tumor rejection antigens are present on cells of a given tumor without mutagenesis. Hence, with reference to the literature, a cell line can be tum⁺, such as the line referred to as "P1", and can be provoked to produce tum⁻ variants. Since the tum⁻ phenotype differs from that of the parent cell line, one expects a difference in the DNA of tum⁻ cell lines as compared to their tum⁺ parental lines, and this difference can be exploited to locate the gene of interest in tum⁻ cells. As a result, it was found that genes of tum⁻ variants such as P91A, 35B and P198 differ from their normal alleles by point mutations in the coding regions of the gene. See Szikora and Sibille, supra, and Lurguin, et al., Cell 58:293–303 (1989). This has proved not to be the case with the TRAs of this invention. These papers also demonstrated that peptides derived from the tum⁻ antigen are presented by the $L^d$ molecule for recognition by CTLs. P91A is presented by $L^d$, P35 by $D^d$ and P198 by $K^d$.

U.S. Pat. No. 5,342,774, the disclosure of which is incorporated by reference, disclosed three members of a family of the genes referred to hereafter as the "MAGE" family of genes. MAGE-1, 2 and 3 are disclosed therein. Also see Traversari, et al., J. Exp. Med 176:1453–1457 (1993); Science 254:1643–147 (1991), the disclosures of which are incorporated by reference. Additional members of the MAGE family have been discovered and are disclosed in, e.g., DePlaen, et al., Immunogenetics 40:360 (1994), and U.S. Pat. No. 5,612,201 to DePlaen, both of which are incorporated by reference. With respect to MAGE-1, in addition to the '774 patent, see e.g. U.S. Pat. No. 5,925,729.

The genes are useful as a source for the isolated and purified tumor rejection antigen precursor and the TRA themselves, either of which can be used as an agent for treating the cancer for which the antigen is a "marker", as well as in various diagnostic and surveillance approaches to oncology, discussed infra. It is known, for example that tum⁻ cells can be used to generate CTLs which lyse cells presenting different tum⁻ cells can be used to generate CTLs which lyse cells presenting different tum⁻ antigens as well as tum⁺ cells. See, e.g., Maryanski, et al., Eur. J. Immunol 12:401 (1982); and Van den Eynde, et al., Modem Trends in Leukemia IX (June 1990), the disclosures of which are incorporated by reference. The tumor rejection antigen precursor may be expressed in cells transfected by the gene, and then used to generate an immune response against a tumor of interest.

In the parallel case of human neoplasms, it has been observed that autologous mixed lymphocyte-tumor cell cultures ("MLTC" hereafter) frequently generate responder lymphocytes which lyse autologous tumor cells and do not lyse natural killer targets, autologous EBV-transformed B cells, or autologous fibroblasts (see Anichini, et al., Immuno. Today 8:385–389 (1987)). This response has been particularly well studied for melanomas, and MLTC have been carried out either with peripheral blood cells or with tumor infiltrating lymphocytes. Examples of the literature in this area including Knuth, et al., Proc. Natl. Acad. Sci. USA 86:2804–2802 (1984); Mukherji, et al., J. Exp. Med. 158: 240 (1983); Hérin, et al., Int. J. Canc. 39:390–396 (1987); Topalian, et al., J. Clin. Oncol 6:839–853 (1988). Stable cytotoxic T cell clones ("CTLs" hereafter) have been derived from MLTC responder cells, and these clones are specific for the tumor cells. See Mukherji, et al., supra, Hérin, et al., supra, Knuth, et al., supra. The antigens recognized on tumor cells by these autologous CTLs do not appear to represent a cultural artifact, since they are found on fresh tumor cells. Topalian, et al., supra; Degiovanni, et al., Eur. J. Immul. 20:1865–1868 (1990). These observations, coupled with the techniques used herein to isolate the genes for specific murine tumor rejection antigen precursors, have led to the isolation of nucleic acid sequences coding for tumor rejection antigen precursors of TRAs presented on human tumors. It is now possible to isolate the nucleic acid sequences which code for tumor rejection antigen precursors, including, but not being limited to those most characteristic of a particular tumor, with ramifications that are described infra.

Additional work has focused upon the presentation of TRAs by the class of molecules known as human leukocyte antigens, or "HLAs". This work has resulted in several unexpected discoveries regarding the field. Specifically, in U.S. Pat. No. 5,405,940, the disclosure of which is incorporated by reference, nonapeptides including a MAGE-3 derived peptide, are taught which are presented by HLA-A1 molecules. The reference teaches that given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

Additional peptides have been identified which consist of amino acid sequences found in MAGE-3, but which bind to different MHC molecules. See, e.g., U.S. Pat. Nos. 5,554, 506, 5,585,46?, 5,591,430 and 6,091,987 which describe peptides which bind to HLA-A2 molecules, and also see U.S. Pat. Nos. 5,965,535, 6,291,430 and 6,369,211, which teach peptides consisting of amino acid sequences found in MAGE-3, which bind to MHC Class II molecules. See, e.g., Tanzarella, et al., Canc. Res. 59:2668–74 (1999), teaching a MAGE-3 based peptide which binds to HLA-B37, as well as Kawashima, et al., Hum Immunol 59:1–14 (1998); Tanako, et al., Cancer Res. 57:4465–68 (1997); Oiso, et al., Int. J. Cancer 81:387–94 (1999), and Herman, et al., Immunogenetics 43:377–83 (1996), which collectively teach MAGE-3 based peptides which bind to HLA-A*0201, A24, B*4402 and B*4403. These papers are all incorporated by reference in their entirety.

It is important to note that different approaches have been taken to identifying the peptides described herein with different ramifications. For example, Gaugler et al., J. Exp. Med. 179:921–930 (1994) and Tanzarella, et al., supra, secured CTLs from melanoma patients following autologous, mixed lymphocyte tumor cell cultures. With respect to the other references cited herein, "motif analysis", using information found in, e.g., Ramensee, et al., Immunogenetics 41:178–228 (1995), incorporated by reference, was applied to the complete sequence of MAGE-3 protein to identify potential HLA molecule binders. These were then tested, and active molecules identified thereby.

This approach, i.e., employing motif analysis, has been found to exhibit a major drawback in that several peptide specific CTL generated using the synthetic peptides, do not recognize HLA matched tumor cells which express MAGE-3 endogenously. There have been two explanations proposed for this. One is that the peptides at issue are not generated efficiently by the cells. The second is that the CTLs obtained using high concentrations of the synthetic peptides have low affinity for the target. See Dahl, et al., J. Immunol 157:239–246 (1996).

MAGE-3 is expressed is about 75% of metastatic melanomas, and in 35–50% of esophageal, head and neck, lung and bladder carcinomas. See, e.g., Gaugler, et al., supra. Boon, et al., "Cancer Vaccines: Cancer Antigens, Shared Tumor Specific Antigens" in Rosenberg, ed., *Principles and*

Practice of The Biologic Therapy of Cancer (Philadelphia, J B Lippincott Williams & Wilkins, 2000), pp. 493–504. Hence, there is interest in having additional methodologies available for identifying peptides consisting of sequences found in MAGE-3, especially those which form complexes with MHC molecules other than those set forth, supra.

A new strategy has been developed for identifying only will processed tumor antigens:dendritic cells transduced with gene MAGE-3 are used as stimulator cells for autologous CD8+ T cells. See, e.g., Luiten, et al., Tissue Antigens 55:149–152 (2000); Chaux, et al., J. Immunol 163:2928–36 (1999); Luiten, et al., Tissue Antigens 56:77–81 (2000); Schultz, et al., Tissue Antigens 57:103–9 (2001), and Van den Eynde: Cancer Immunity 2001: www.cancerimmmunity.org/peptidedatabase/tcellepitopes.htm:, all of which are incorporated by reference, for examples of the application of this technique, with identification of relevant antigenic peptides.

Marsh, et al., *The HLA Factsbook*, (Academic Press, 2000), incorporated by reference, supplements older information on MHC binding peptides, such as that provided by Ramensee, supra. Relevant here is Marsh's discussion of the MHC molecule HLA-B18 which is not presented in Ramensee. Marsh, et al. note that approximately 5–6% of black and caucasian populations present HLA-B18 alleles (seven have been identified). With respect to binding peptides, rather than presenting a traditional anchor pattern of at least two well defined amino acids, one of which is at the C terminus, the only "common denominator" observed by Marsh, et al. is the amino acid "E" at position 2; however, of the three T cell epitopes disclosed by Marsh, et al., only one presents E at second position. None of the peptides are based upon cancer associated molecules.

As will be seen herein, it has now been observed that a MAGE-3 peptide, previously identified as a T cell epitope for HLA-B44, is also an epitope for HLA-B18. This, and the ramifications of this observation, constitute the invention, which is elaborated upon in the detailed description which follows.

EXAMPLE 1

This example describes the construction of an adenovirus based vector which expresses MAGE-3, and the infection of monocyte derived, dendritic cells thereby.

The recombinant adenovirus, referred to as "Adeno.MAGE-3," was generated via in vivo homologous recombination in 293-EBNA cells, described by Graham, et al., J. Gen. Virol 36:59–72 (1977), that had been transformed with an adenovirus of type V (ATCC:CRL 1573). These 293-EBNA cells were typed as HLA-A3, B7, Cw7 and were positive for expression of MHC Class I expression, when tested with Class I specific monoclonal antibody W6/32, as described by Parham, et al., J. Immunol 123:342–9 (1979).

Adeno.MAGE-3 was generated via overlapping adenoviral sequences in pAd-CMVIcpA-MAGE-3, and restriction cleaved viral DNA of defective strain dl324, in accordance with Stratford-Perricaudet, et al., J. Clin. Invest 90:626-630 (1992), incorporated by reference.

To elaborate, the 293 cells were cotransfected with 5 µg each of linearized plasmid pAd-CMVIcpA-MAGE-3 and the large, ClaI DNA fragment of dl324.

Recombinant adenovirus was plaque purified, and the presence of the transgene was assessed via restriction analysis. Recombinant adenovirus was propagated in 293 cells, purified by double cesium chloride density centrifugation, and dialyzed extensively. Viral stocks were stored in aliquots with 10% glycerol, at −80° C., and were titred by plaque assay, using 293 cells, as necessary.

The dendritic cells were obtained by starting with peripheral blood from a hemochromatosis patient, as a standard buffy coat preparation. The preparations were laid down on a 15 ml Lymphoprep layer, in 50 ml tubes. Contamination by platelets was minimized by centrifuging the tubes at 1,000 rpm for 20 minutes at room temperature. The top 20–25 mls were removed, as these contain most of the platelets and tubes were then centrifuged at 1500 rpm for 20 minutes, at room temperature. The interphase containing PBMCs were harvested, and washed at least 3 times in cold, phosphate buffer solution containing 2 mM EDTA, so as to eliminate the remaining platelets.

Autologous dendritic cells were then generated by depleting PBMCs from T lymphocytes, by rosetting with sheep erythrocytes, that had been treated with 2-aminoethylisothiouronium. Any rosetted T cells were then treated with $NH_4Cl$ (160 mM) to lyse sheep erythrocytes, and were then washed. The CD 8+ T lymphocytes were isolated from rosetted T cells via positive selection, using an anti-CD8 monoclonal antibody, coupled to magnetic microbeads. Cells were sorted through a magnet, and frozen until needed.

These purified, dendritic cells were infected with Adeno.MAGE-3, by combining $3\times10^6$ cells with the adenovirus, at a multiplicity of infection ("MOI" hereinafter) of 30, in 200 µl of complete RPMI medium at 37° C., under 5% $CO_2$. Infected dendritic cells were washed after 2 hours.

EXAMPLE 2

This example describes how the adenovirus infected dendritic cells were used to stimulate autologous CD8+ T lymphocytes.

As noted, supra, CD8+ cells had been isolated, and frozen. The day before stimulation experiments, the CD8+ cells were thawed and grown overnight in IMDM, supplemented with 10% human serum, AAG and antibiotics, (complete IMDM), together with 10 U/ml of IL-2.

Autologous responder CD8+ T lymphocytes were then mixed ($1.5\times10^5$ cells), with infected dendritic cells ($3\times10^4$), in U bottomed microwells in 200 µl of complete IMDM, together with IL-6 (1000 U/ml), and IL-12 (10 ng/ml). On days 7, 14 and 21, autologous dendritic cells were thawed, infected with the Adeno.-MAGE-3 vector as described supra, and used for stimulating the responder cells, in medium supplemented with IL-2 (10 U/ml), and IL-7 (5 ng/ml).

An aliquot of each of the T cell microcultures was tested for lytic activity on day 28, as described in the example which follows.

EXAMPLE 3

The CD8+ cells stimulated in example 2 were used in this example. As indicated, they were tested for lytic activity on day 28.

The target of the CD8+ cells was autologous, EBV-B cells that had been infected with either vaccinia-MAGE-3, or control vaccinia virus.

An EBV-B transformed B cell line was derived from the blood cells of the hemochromatosis blood donor referred to supra, by culturing isolated B cells with 20% of a supernatant of EBV-transformed, B95–8 cells, available from the American Type Culture Collection (CRL 1612), in the presence of 1 µg/ml of cyclosporin A. The cells were cultured in Iscove's modified Dulbecco medium, supplemented with 10% fetal calf serum, 0.24 mM L-asparagine, 0.55 mM L-arginine, and 1.5 mM L-glutamine, as well as 100 U/ml penicillin and 100 µg/ml streptomycin.

In order to transfect the EBV-B cells, a readily available vaccinia-MAGE-3 was used. Virus particles were sonicated for 1 minute before use. Following sonication, $2 \times 10^6$ EBV-B cells were combined with the particles for 2 hours, at an MOI of 20, in 150 µl of complete RPMI medium. The infected cells were washed, labelled with 100 µl Ci of $Na(^{51}Cr)O_4$, and were then added to the $CD8^+$ cells described supra, at an effector:target ratio of 40:1.

A microculture of the $CD8^+$ cells which exhibited anti-MAGE-3 reactivity on the EBV-B cells transfected with vaccinia-MAGE-3 in a standard, $^{51}Cr$ release assay was taken, and the cells were cloned in U-bottomed microplates via limiting dilution, in complete IMDM supplemented with IL-2 (50 U/ml), and 15 µg/ml gentamycin. These T cells were stimulated with $4 \times 10^3$ irradiated (100 Gy) EBV-B cells that had been infected with Yersinia.MAGE-$3_{1-196}$, and $4 \times 10^3$ EBV-B cells that had been infected with Yersinia.MAGE-$3_{147-314}$. Yersinia constructs were used to avoid T cell responses to adenovirus proteins. Allogenic EBV-B cells ($1 \times 10^4$ LG2-EBV-B cells per well) were used as feeder cells.

These Yersinia transfected EBV-B cells were prepared, using strain MRS40(pABL403), as described by Boland, et al., Infect. Immun 66:1878–84 (1988), incorporated by reference. The strain encodes mutated or truncated toxic Yop proteins, but maintains its ability to translocate proteins in fusion with truncated YopE into the cytosol of eukaryotic cells, but does not elicit cytotoxicity, and is used as a vector to inject protein into the cytosol of eukaryotic cells.

A first construct containing amino acids 1–196 of MAGE-3 was inserted, in frame, with a sequence encoding the first 130 amino acids of YopE, into vector pMS621, described by Gary, et al., Mol. Microbiol 14:583–94 (1994), incorporated by reference. Similarly, a construct was made which encoded amino acids 147–314 of MAGE-3. Either of these plasmids were electroporated into E. coli strain SM10, and then mobilized into Yersinia enterocolitica MRS40. The recombinant MRS40 clones were selected on agar containing medium, supplemented with 35 µg/ml nalidixic acid, 1 mM sodium m-arsenite, and 12 µg/ml of chloramphenicol, in accordance with Neyt, et al., J. Bacteriol 179:612–9 (1997). Colonies containing Yersinia constructs encoding the MAGE-3 constructs described supra were grown overnight at 28° C. in LB medium, and was then diluted to obtain an OD of 0.2 at 600 nm, and was then cultured at 28° C. for about 2 hours. Bacteria were washed in 0.9% NaCl, and resuspended, at $10^8$ bacteria per ml, in 0.9% NaCl, assuming that a culture giving and $OD_{600}$ equals one containing $5 \times 10^8$ bacteria per ml.

Following this, EBV-B cells that had been irradiated at 100 Gys were resuspended at $10^6$ cells in 3.8 ml of RPMI, without antibiotics, supplemented with 10% FCS and AAG. Then, 200 µl of the bacterial suspension were added, and after two hours of infection, the cells were incubated for an additional 2 hours with 30 µg/ml gentamycin, and then were washed, three times, prior to use as stimulator cells, as described supra.

A CTL clone was obtained, which will be referred to thereafter as CTL22.

EXAMPLE 4

The MAGE-3-encoding retroviral vector plasmids MFG-MAGE-3 was introduced into PhoenixAMPHO packaging cells by transfection. The transfection procedure is a modification of the calcium phosphate-mediated transfection protocol of Graham and van der Eb, Virology 52(2):456:67 (1973), incorporated by reference. Twenty-four hours prior to transfection, PhoenixAMPHO cells were plated in cell growth medium in a 75 cm² tissue culture flask. After adding the cells, the flask was gently shaken forward and backward to distribute cells evenly about the flask bottom. The cells were incubated at 37° C. in a 5% $Co_2$ atmosphere. At the time of transfection, when the cells should have reached a confluence of 70–80%, the medium was removed and was replaced by 14 ml fresh PhoenixAMPHO cell growth medium containing 25 mM chloroquine. A transfection cocktail was prepared in a 50 ml tube by adding 40 µg retroviral vector plasmid DNA to water and diluting to 1575 µl final volume. To this DNA solution, 225 µl of 2 M $CaCl_2$ was added. Then 1800 µl of 2×HeBS (50 mM HEPES, 10 mM KCl, 12 mM dextrose, 280 mM NaCl and 1.5 mM $Na_2HPO_4$ dissolved in distilled water, filtered through 0.2 µm filter and stored at −20° C.) was added dropwise to the $DNA/CaCl_2$ solution by bubbling vigorously for 15 seconds with an automatic pipette. The $DNA/CaCl_2/HeBS$ mix was added immediately and dropwise onto the cells and the flask was gently swirled to ensure uniform mixing of DNA/ $CaPO_4$ particles. The cells were incubated at 37° C./5% $CO_2$ for 7 to 9 hours and the chloroquine-containing medium was changed for fresh PhoenixAMPHO cell growth medium. Approximately 24 hours prior to the harvest of the retroviral supernatant, the PhoenixAMPHO medium was removed and gently replaced by 9 ml of ID medium containing only 2.5% FCS. The retroviral supernatant was harvested 48 hours after transfection by removing the medium from the cells and filtering through a 0.45 µm filter to remove cell debris. After harvest and filtration, the virus-containing medium was kept on ice, aliquoted in appropriate volumes in 15 ml polypropylene tubes and stored at −80° C.

Target cells were resuspended in 60 mm tissue culture plates at a density of $10^6$ cells in 4 ml of infection cocktail containing 50% viral supernatant in growth medium and 6 µg/ml of protamine sulfate. The plates were centrifuged for 2 hours at 32° C. and 1200 rpm, followed by another 2 hours of incubation in a humidified incubator at 37° C. Cells were then transferred to 4 ml of growth medium. This transduction cycle was carried out immediately after plating the cells and was repeated at 24 and 48 hours.

EXAMPLE 5

These experiments were designed to determine the peptide recognized by CTL22. A set of 16 amino acid long peptides was prepared, which overlapped by 12 amino acids, and covered the entire MAGE-3 amino acid sequence. Peptides were prepared using standard solid phase procedures.

Autologous EBV-B cells were $^{51}Cr$ labelled, and incubated with each peptide for 30 minutes at 37° C., at a concentration of 1 µg/ml, and were tested for lysis in $^{51}Cr$ release assays, as described supra, with CTL22 at an effector:target ratio of 10:1. $^{51}Cr$ release was measured after 4 hours. The peptide consisting of amino acids 167–182 of MAGE-3:

MEVDPIGHLYIFATCL (SEQ ID NO: 1) scored positive. As a result, a number of shorter peptides based upon this peptide were tested, in the same assay. The peptide consisting of the first 10 amino acids of SEQ ID NO: 1 was the most efficient sensitizing agent. Half maximal lysis was obtained at a peptide concentration of 2 nM. This is within the range reported for other antigenic MAGE peptides, which is 0.05 to 100 nM. See Luiten, et al., Tissue Antigens 55:149–152 (2000); Chaux, et al., J. Immunol 163:2928–36 (1999); Schultz, et al., Tissue Antigens 57:103–9 (2001); Traversari, et al., J. Exp. Med. 176:1453–7 (1992); van der Bruggen, et al., Eur. J. Immunol 24:2134–40 (1994).

EXAMPLE 6

These examples were designed to determine the MHC molecule responsible for presenting the active peptide.

The cell donor had been HLA typed previously as HLA-A2, A3, B*1801, B*1501101, Cw*0304, and Cw*0501 positive. In a set of preliminary experiments, autologous EBV-B cell lines which expressed A2 or A3 were pulsed with the active peptide, and were not lysed by CTL22. This, of course, suggested that one of the HLA-B or C molecules was responsible for peptide presentation.

As reported, supra, 293-EBNA was typed as HLA-A3, B7, Cw7, so it was chosen as the target cell for the experiments which follow.

The 293-EBNA cells were distributed (5×104 cells), in flat bottomed microwells, and were transfected, one day later, with MAGE-3 cDNA inserted into pcDNAI/Amp, and cDNA encoding one of the HLA-B and C molecules supra, also inserted in pcDNA3. The transfection utilized 5×10$^4$ 293-EBNA cells, and 50 ng of each of the cDNA molecules, together with 1 μl of lipofectamine. One day after transfection, 3000 CTL22 cells were added, in a total volume of 150 μl of complete IMDM, supplemented with 25 U/ml of IL-2. A TNF secretion assay was carried out, in accordance with Traversari, et al., Immunogenetics 35:145–152 (1992) incorporated reference, except that 20 mM of LiCl were added during incubation with supernatant of TNF sensitive, WEHI-164c13 cells. See Beyaert, et al., Proc. Natl. Acad Sci USA 86:9494–8 (1989); Espevik, et al., J. Immunol Meth. 95:99–105 (1986).

Only the cells which had been transfected with both MAGE-3 and HLA-B*1801 stimulated CTL22 to produce TNF.

In a follow-up experiments, cell line LCL 721.221 was tested, because it is an EBV derived cell line that does not express HLA Class-I molecules on its surface. Five million cells were electroporated with 50 ng of pcDNA3 containing the coding sequence of either B*1801 or B*1501101, using a single pulse at 260 volts, 1575 ohms, and 1,050 farads. Cells were selected based upon resistance to 1.5 mg/ml geniticin, and were also tested and isolated for HLA expression via flow cytometry and labeling with anti-HLA-A, -B, or -C antibody B1.23.2, in accordance with Rebai, et al., Tissue Antigens 22:107–117 (1983), incorporated by reference.

The transfectants were then incubated with the active peptide in a $^{51}$Cr lysis assay as described supra. Only HLA-B*1801 cells were lysed.

EXAMPLE 7

The data, supra, show how dendritic cells were used to activate CTL22. These experiments were designed to determine if tumor cells process the antigen.

Two melanoma cell lines were isolated from HLA-B*1801 positive patients, which also expressed MAGE-3. The experiments were carried our as described, supra. One line, i.e., LB-24 MEL, was lysed slightly, which the other was not.

It is well known that many tumors downregulate or lose HLA expression. See, e.g., Garrido, et al., Adv. Cancer Res 67:155–95 (1995); Ferrine, et al., Immunol Today 16:487–94 (1995). Hence, experiments were carried out to determine if the unaffected line could be lysed by loading it with peptide. The results indicated poor lysis, strongly suggesting the HLA defect referred to supra; however it is well known that gamma interferon treatment can result in upregulation of HLA in some cells. When gamma interferon was added to the two lines, without the addition of peptide, the lysis increased confirming the role of HLA-B*1801 as presenting molecule.

The foregoing disclosure sets forth various features of the invention. These include isolated peptides which are processed to peptides that form immunogenic complexes with HLA-B18 molecules. The peptides of the invention comprise the first 10 amino acids of SEQ ID NO: 1, i.e.:

MEVDPIGHLY concatenated to from 1 to 30 additional amino acids at the N (Met) or C (Tyr) terminus, preferably from 5–10 additional amino acids, such as the peptide of SEQ ID NO: 1. Preferably, the concatenated amino acids are identical to the amino acid sequence which precedes Met or follows Tyr in the full length amino acid sequence of MAGE-3, but the concatenated amino acids also accommodate variations, such as conservative substitutions, deletions, additions and so forth. The peptides of the invention possess the functional properties of being taken up by antigen presenting cells, such as dendritic cells, and being processed to the 10 amino acid sequence described supra.

Preferably, the cells which take up the peptides are cells which present HLA-B18 molecules on their surface. As was noted, supra, the 10 amino acid peptide referred to herein is also presented by HLA-B44 cells, so the cells may be those which are positive for either HLA-B18 or HLA-B44, or both.

Also a feature of this invention are isolated cytolytic T cells which are specific for complexes of HLA-B18 molecules and the 10 amino acid sequence referred to supra, which do not recognize other complexes, including complexes of the sequence and different HLA molecules. As was shown, supra, such cytolytic T cells can be prepared using standard methodologies, including those described herein.

In connection with the cytolytic T cell lines of the invention, various methods can be used to identify and to secure these. Such methodologies include, i.e., FACS or other analytical methods, preferably in combination with molecules, such as tetrameric compounds of avidin or streptavidin, biotin, and HLA/peptide complexes, to identify relevant CTLs from samples.

The ability of the peptides to form recognizable complexes makes them useful as therapeutic agents in conditions such as cancer, including melanoma, lung, breast, head and neck, and other cancer types, such as those described in, e.g., Principals and Practic of The Biologic Therapy of Cancer (Lippincott Williams and Wilkens, 3$^{rd}$ ed., 2000), p. 499, incorporated by reference, where the peptide forms a complex with the HLA molecule, leading to recognition by a CTL, and lysis thereby. As was shown, supra, CTLs which recognize the complexes occur naturally in patients, so administration of the peptide of the invention to an HLA-B18 positive subject in need of a cytolytic T cell in response is another feature of the invention. Such subjects may be, e.g., cancer patients, such as melanoma patients. Such patients may receive the peptide of the invention, or "cocktails" which comprise more than one peptide, as long as the peptide cocktail includes the peptide of the invention. The peptide component of such cocktails may consist of the peptides described herein, or may combine some peptides disclosed herein with other peptides known in the art, such as the following, which bind to Class I or Class II MHC.

| PEPTIDE SEQUENCE | ANTIGEN | HLA | SEQ ID NO: |
|---|---|---|---|
| YMDGTMSQV | TYROSINASE | A2 | 2 |
| MLLAVLYCL | TYROSINASE | A2 | 3 |
| ELAGIGILTV | MELAN-A | A2 | 4 |
| IMPKAGLLI | MAGE-A3 | A2 | 5 |
| FLWGPRALV | MAGE-A3 | A2 | 6 |
| VRIGHLYIL | MAGE-A6 | Cw7 | 7 |
| YLQLVFGIEV | MAGE-A2 | A2 | 8 |
| FLWGPRALV | MAGE-A12 | A2 | 9 |
| VLPDVFIRC(V) | GnTV | A2 | 10 |
| KASPKIFYV | SSX2 | A2 | 11 |
| GLYDGMEHL | MAGE-A10 | A2 | 12 |
| EVDPIGHLY | MAGE-A3 | A1 | 13 |
| SLLMWITQC | NY-ESO-1 | A2 | 14 |
| IMPKAGLLI | MAGE-A3 | A24 | 15 |
| EVDPIGHLY | MAGE-A3 | B35 | 16 |
| GVYDGREHTV | MAGE-A4 | A2 | 17 |
| EADPTGHSY | MAGE-A1 | A1,B35 | 18 |
| SEIWRDIDF | TYROSINASE | B44 | 19 |
| LPSSADVEF | TYROSINASE | B35 | 20 |
| MEVKPIGHLY | MAGE-A3 | B18,B44 | 21 |
| YRPRPRRY | GAGE-1,2,8 | Cw6 | 22 |
| LAMPFATPM | NY-ESO-1 | Cw3 | 23 |
| ARGPESRLL | NY-ESO-1 | Cw6 | 24 |
| YYWPRPRRY | GAGE-3,4,5,6,7 | A29 | 25 |
| AARAVFLAL | BAGE-1 | Cw16 | 26 |
| TQHEVQENYLEY | MAGE-A3 | DP4 | 27 |
| SLLMWITQCFL | NY-ESO-1 | DP4 | 28 |
| AELVHFLLLKYRAR | MAGE-A3 | DR13 | 29 |
| LLKYRAREPVTKAE | MAGE-A3, A6,A2 | DR13 | 30 |
| AELVHFLLLKYRAR | MAGE-A-12 | DR13 | 31 |
| EYVIKVSARVRF | MAGE-A1 | DR15 | 32 |
| LLKYRAREPVTKAE | MAGE-A1 | DR13 | 33 |
| PGVLLKEFTVSGNILTIRLT | NY-ESO-1 | DR4 | 34 |
| AADHRQLQLSISSCLQQL | NY-ESO-1 | DR4 | 35 |

In an especially preferred embodiment, one administers a cocktail of peptides based upon the HLA profile of the subject being treated. Based upon known Class I peptide binding motifs, such as those set forth by Ramensee, et al., supra, peptides such as those set forth at SEQ ID NOS: 2–35 would be expected to bind to other HLA-Class I or II alleles, such as HLA-A1, A3, B7, B8, B15, B27, B44, B51 in addition to HLA-A2, and subtypes thereof. Further, if appropriate, one or more peptides which bind to HLA-A2, HLA-B7, HLA-Cw6 and so forth, can be admixed, preferably in the presence of an adjuvant like GM-CSF, alum, or another adjuvants well known to the art, such as CpG. See U.S. Pat. Nos. 6,339,068; 6,239,116; 6,207,646 and 6,194,388, all of which are incorporated by reference. Also possible as therapeutic agents are peptide pulsed, autologous dendritic cells. See, e.g., Jonuleit, et al., Int. J. Cancer 93(2):243–51 (2001); Schuler-Thurner, et al., J. Immunol 165(6):3492–6 (2000); Thurner, et al., J. Exp. Med. 190(11):1669–78 (1999), all of which are incorporated by reference and show, e.g., the use of peptide pulsed dendritic cells as vaccines and as adjuvants. Such combinations of peptides, in the form of compositions, are another feature of the invention, either alone or in combination with such adjuvants. Similarly, one can administer cytolytic T cells specific for the peptide/HLA-B18 complexes, such as autologous CTLs, which can be prepared as described in the preceding examples. These CTLs, which are specific for complexes of the first 10 amino acids of SEQ ID NO: 1 and HLA-B18, and no other complexes, are a further feature of the invention.

Yet a further feature of the invention are nucleic acid molecules which consist of nucleotide sequences that encode the peptide of the invention. Such nucleic acid molecules may be used to encode the peptides of the invention, and may be combined into expression vectors, operably lined to a promoter. More than one sequence can be combined in such expression vectors, as can nucleic acid molecules which encode HLA-B18 molecules. The constructs can be used to transfect cells, so as to generate the CTLs, or for administration to subjects in need of a cytolytic T cell response or augmenting of a pre-existing T cell response. Such administration could be one of, e.g., administering vector constructs as described, heterologous expression vectors, peptides or recombinant proteins, such as the full length proteins, preferably in recombinant form, from which one or more of the peptides are derived as discussed supra.

The invention also relates to the use of the peptides, CTLs, and other, immunologically active components, such as antibodies, to diagnose pathological conditions such as cancer, melanoma in particular. As was shown, supra, MAGE-3 is expressed in cancer cells and the presence of complexes of the first 10 amino acids of SEQ ID NO: 1 and HLA-B18 is indicative of a pathological condition. By determining the interaction of the immunologically active component and the complex (by way of, e.g., antibody binding, TNF release, cell lysis, etc.), one can diagnose the pathology, or even determine the status of the pathology via comparing a value to a pre-existing value for the same parameter.

The invention also embraces functional variants of the MAGE-3 HLA class I binding peptide. As used herein, a "functional variant" or "variant" of a MAGE-3 HLA class I binding peptide is a peptide which contains one or more modifications to the primary amino acid sequence of MAGE-3 HLA class I binding peptide and retains the HLA class I and T cell receptor binding properties disclosed herein. Modifications which create a MAGE-3 HLA class I binding peptide functional variant can be made for example 1) to enhance a property of a MAGE-3 HLA class I binding peptide, such as peptide stability in an expression system or the stability of protein-protein binding such as HLA-peptide binding; 2) to provide a novel activity or property to a MAGE-3 HLA class I binding peptide, such as addition of an antigenic epitope or addition of a detectable moiety; or 3) to provide a different amino acid sequence that produces the same or similar T cell stimulatory properties. Modifications to a MAGE-3 HLA class I binding peptide can be made a nucleic acid which encodes the peptide, and can include deletions, point mutations, truncations, amino acid substitutions and additions of amino acids. Alternatively, modifications can be made directly to the polypeptide, such as by cleavage, addition of a linker molecule, addition of a detectable moiety, such as biotin, addition of a fatty acid, substitution of one amino acid for another and the like. Modifications also embrace fusion proteins comprising all of part of the MAGE-3 HLA class I binding peptide amino acid sequence.

The amino acid sequence of MAGE-3 HLA class I binding peptides may be of natural or non-natural origin, that is, they may comprise a natural MAGE-3 HLA class I binding peptide molecule or may comprise a modified sequence as long as the amino acid sequence retains the ability to stimulate T cells when presented and retains the property of binding to an HLA class I molecule such as an HLA-B18 or B44 molecule. For example, MAGE-3 HLA class I binding peptides in this context may be fusion proteins of a MAGE-3 HLA class I binding peptide and unrelated amino acid sequences, a synthetic peptide of amino acid sequences shown in SEQ ID NO: 1 or the sequence MEVDPIGHLY, labeled peptides, peptides isolated from patients with a MAGE-3 expressing cancer, peptides isolated from cultured cells which express MAGE-3, peptides coupled to nonpeptide molecules (for example in certain drug delivery systems) and other molecules which include the amino acid sequence of MEVDPIGHLY.

Preferably, MAGE-3 HLA class I binding peptides are non-hydrolyzable. To provide such peptides, one may select MAGE-3 HLA class I binding peptides from a library of non-hydrolyzable peptides, such as peptides containing one or more D-amino acids or peptides containing one or more non-hydrolyzable peptide bonds linking amino acids. Many non-hydrolyzable peptide bonds are known in the art, along with procedures for synthesis of peptides containing such bonds. Non-hydrolyzable bonds include -psi[CH.sub.2NH]-reduced amide peptide bonds, -psi[COCH.sub.2]- ketomethylene peptide bonds, -psi[CH(CN)NH]-(cyanomethlylene) amino peptide bonds, -psi[CH.sub.2CH(OH)]-hydroxyethylene peptide bonds, -psi[CH.sub.2O]-peptide bonds, and -psi[CH.sub.2S]-thiomethylene peptide bonds. Methods for determining such functional variants are provided in U.S. Pat. No. 6,087,441, incorporated by reference.

If a variant involves a change to an amino acid of SEQ ID NO: 1 or the sequence MEVDPIGHLY, functional variants of the MAGE-3 HLA class I binding peptide having conservative amino acid substitutions typically will be preferred, i.e., substitutions which retain a property of the original amino acid such as charge, hydrophobicity, conformation, etc. Examples of conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. Methods for identifying functional variants of the MAGE-3 HLA class I binding peptides are provided in a U.S. Pat. Nos. 6,277,956 and 6,326,200 and published PCT application WO0136453 (U.S. patent application Ser. Nos. 09/440,621, 09/514,036, 09/676,005), all of which are incorporated by reference.

Thus methods for identifying functional variants of a MAGE-3 HLA class I binding peptide are provided. In general, the methods include selecting a MAGE-3 HLA class I binding peptide, an HLA class I binding molecule which binds the MAGE-3 HLA class I binding peptide, and a T cell which is stimulated by the MAGE-3 HLA class I binding peptide presented by the HLA class I binding molecule. In preferred embodiments, the MAGE-3 HLA class I binding peptide comprises the amino acid sequence of amino acids 6–14 of SEQ ID NO: 1. More preferably, the peptide consists of the amino acid sequence of MEVDPIGHLY. A first amino acid residue of the MAGE-3 HLA class I binding peptide is mutated to prepare a variant peptide. Any method for preparing variant peptides can be employed, such as synthesis of the variant peptide, recombinantly producing the variant peptide using a mutated nucleic acid molecule, and the like.

The binding of the variant peptide to HLA class I binding molecule and stimulation of the T cell are then determined according to standard procedures wherein binding of the variant peptide to the HLA class I binding molecule and stimulation of the T cell by the variant peptide presented by the HLA class I binding molecule indicates that the variant peptide is a functional variant. For example, the variant peptide can be contacted with an antigen presenting cell which contains the HLA class I molecule which binds the MAGE-3 peptide to form a complex of the variant peptide and antigen presenting cell. This complex can then be contacted with a T cell which recognizes the epitope formed by the MAGE-3 HLA class I binding peptide and the HLA class I binding molecule. T cells can be obtained from a patient having a condition characterized by expression of MAGE-3. Recognition of variant peptides by the T cells can be determined by measuring an indicator of T cell stimulation.

Binding of the variant peptide to the HLA class I binding molecule and stimulation of the T cell by the epitope presented by the complex of variant peptide and HLA class I binding molecule indicates that the variant peptide is a functional variant. The methods also can include the step of comparing the stimulation of the T cell by the epitope formed by the MAGE-3 HLA class I binding peptide and the HLA class I molecule, stimulation of the T cell as a determination of the effectiveness of the stimulation of the T cell by the epitope. By comparing the epitope involving the epitope formed by the functional variant with the MAGE-3 HLA class I binding peptide, peptides with increased T cell stimulatory properties can be prepared.

Variants of the MAGE-3 HLA class I binding peptides prepared by any of the foregoing methods can be sequenced, if necessary, to determine the amino acid sequence and thus deduce the nucleotide sequence which encodes such variants.

Other features of the invention will be clear to the skilled artisan, and need not be reiterated herein.

We claim:

1. An isolated cytolytic T lymphocyte which recognizes complexes of HLA-B18 molecules and the peptide consisting of the first 10 amino acids of SEQ ID NO: 1, wherein said isolated cytolytic T lymphocyte does not recognize any other complexes of MHC molecules and peptides.

2. A method for determining if a subject who is HLA-B18 and is suffering from a cancer whicb expresses MAGE-3, comprising:
   incubating a sample of cells taken from said subject with an immunologically active agent which recognizes complexes of an HLA-B18 molecule and the first 10 amino acids of SEQ ID NO: 1, and
   determining interaction between said immunologically active agent and said cells in said sample as a determination of cancer in said subject.

3. The method of claim 2, wherein said immunologically active agent is a cytolytic T lymphocyte.

4. The method of claim 3, comprising determining lysis of cells by said cytolytic T lymphocyte.

5. The method of claim 3, comprising measuring tumor necrosis factor release by said cytolytic T lymphocyte.

6. The method of claim 2, wherein said immunologically active agent is an antibody.

7. An isolated peptide consisting of from about 11 to about 40 amino acids found in the amino acid seciwence of MAGE-3, wherein the amino acid sequence of said peptide consists of
   MEVDPIGHLY (amino acids 1–10 of SEQ ID NO:1) concatenated to from 1 to about 30 additional amino acids at Met or Tyr, wherein said peptide is processed by an antigen presenting cell to a peptide consisting of
   MEVDPIGHLY (amino acids 1–10 of SEQ ID NO:1).

8. The isolated peptide of claim 7, consisting of the amino acid sequence set forth in SEQ ID NO: 1.

9. An isolated nucleic acid molecule consisting of a nucleotide sequence which encodes the isolated peptide of claim 7.

10. An isolated nucleic acid molecule which consists of a nucleotide sequence which encodes MEVDPIGHLY(amino acids 1–10 of SEQ ID NO:1).

11. A composition comprising
   (i) isolated peptide MEVDPIGHLY(amino acids 1–10 of SEQ ID NO:1), and
   (ii) at least one additional isolated peptide as set forth in SEQ ID NOS: 1–28, 32, 34, and 35.

* * * * *

```
                           SEQUENCE LISTING

<160> NUMBER OF SEQ ID NOS: 35

<210> SEQ ID NO 1
<211> LENGTH: 16
<212> TYPE: PRT
<213> ORGANISM: H. sapiens
<220> FEATURE:

<400> SEQUENCE: 1

Met Glu Val Asp Pro Ile Gly His Leu Tyr Ile Phe Ala Thr Cys Leu
 1               5                  10                  15

<210> SEQ ID NO 2
<211> LENGTH: 9
<212> TYPE: PRT
<213> ORGANISM: H. sapiens
<220> FEATURE:

<400> SEQUENCE: 2

Tyr Met Asp Gly Thr Met Ser Gln Val
 1               5

<210> SEQ ID NO 3
<211> LENGTH: 9
<212> TYPE: PRT
<213> ORGANISM: H. sapiens
<220> FEATURE:

<400> SEQUENCE: 3

Met Leu Leu Ala Val Leu Tyr Cys Leu
 1               5

<210> SEQ ID NO 4
<211> LENGTH: 10
<212> TYPE: PRT
<213> ORGANISM: H. sapiens
<220> FEATURE:

<400> SEQUENCE: 4

Glu Leu Ala Gly Ile Gly Ile Leu Thr Val
 1               5                  10

<210> SEQ ID NO 5
<211> LENGTH: 9
<212> TYPE: PRT
<213> ORGANISM: H. sapiens
<220> FEATURE:

<400> SEQUENCE: 5

Ile Met Pro Lys Ala Gly Leu Leu Ile
 1               5

<210> SEQ ID NO 6
<211> LENGTH: 9
<212> TYPE: PRT
<213> ORGANISM: H. sapiens
<220> FEATURE:

<400> SEQUENCE: 6

Phe Leu Trp Gly Pro Arg Ala Leu Val
 1               5
```

```
<210> SEQ ID NO 7
<211> LENGTH: 9
<212> TYPE: PRT
<213> ORGANISM: H. sapiens
<220> FEATURE:

<400> SEQUENCE: 7

Val Arg Ile Gly His Leu Tyr Ile Leu
 1               5

<210> SEQ ID NO 8
<211> LENGTH: 10
<212> TYPE: PRT
<213> ORGANISM: H. sapiens
<220> FEATURE:

<400> SEQUENCE: 8

Tyr Leu Gln Leu Val Phe Gly Ile Glu Val
 1               5                  10

<210> SEQ ID NO 9
<211> LENGTH: 9
<212> TYPE: PRT
<213> ORGANISM: H. sapiens
<220> FEATURE:

<400> SEQUENCE: 9

Phe Leu Trp Gly Pro Arg Ala Leu Val
 1               5

<210> SEQ ID NO 10
<211> LENGTH: 10
<212> TYPE: PRT
<213> ORGANISM: H. sapiens
<220> FEATURE:

<400> SEQUENCE: 10

Val Leu Pro Asp Val Phe Ile Arg Cys Val
 1               5                  10

<210> SEQ ID NO 11
<211> LENGTH: 9
<212> TYPE: PRT
<213> ORGANISM: H. sapiens
<220> FEATURE:

<400> SEQUENCE: 11

Lys Ala Ser Pro Lys Ile Phe Tyr Val
 1               5

<210> SEQ ID NO 12
<211> LENGTH: 9
<212> TYPE: PRT
<213> ORGANISM: H. sapiens
<220> FEATURE:

<400> SEQUENCE: 12

Gly Leu Tyr Asp Gly Met Glu His Leu
 1               5

<210> SEQ ID NO 13
<211> LENGTH: 9
<212> TYPE: PRT
<213> ORGANISM: H. sapiens
<220> FEATURE:
```

```
<400> SEQUENCE: 13

Glu Val Asp Pro Ile Gly His Leu Tyr
1               5

<210> SEQ ID NO 14
<211> LENGTH: 9
<212> TYPE: PRT
<213> ORGANISM: H. sapiens
<220> FEATURE:

<400> SEQUENCE: 14

Ser Leu Leu Met Trp Ile Thr Gln Cys
1               5

<210> SEQ ID NO 15
<211> LENGTH: 9
<212> TYPE: PRT
<213> ORGANISM: H. sapiens
<220> FEATURE:

<400> SEQUENCE: 15

Ile Met Pro Lys Ala Gly Leu Leu Ile
1               5

<210> SEQ ID NO 16
<211> LENGTH: 9
<212> TYPE: PRT
<213> ORGANISM: H. sapiens
<220> FEATURE:

<400> SEQUENCE: 16

Glu Val Asp Pro Ile Gly His Leu Tyr
1               5

<210> SEQ ID NO 17
<211> LENGTH: 10
<212> TYPE: PRT
<213> ORGANISM: H. sapiens
<220> FEATURE:

<400> SEQUENCE: 17

Gly Val Tyr Asp Gly Arg Glu His Thr Val
1               5                   10

<210> SEQ ID NO 18
<211> LENGTH: 9
<212> TYPE: PRT
<213> ORGANISM: H. sapiens
<220> FEATURE:

<400> SEQUENCE: 18

Glu Ala Asp Pro Thr Gly His Ser Tyr
1               5

<210> SEQ ID NO 19
<211> LENGTH: 9
<212> TYPE: PRT
<213> ORGANISM: H. sapiens
<220> FEATURE:

<400> SEQUENCE: 19

Ser Glu Ile Trp Arg Asp Ile Asp Phe
1               5
```

-continued

<210> SEQ ID NO 20
<211> LENGTH: 9
<212> TYPE: PRT
<213> ORGANISM: H. sapiens
<220> FEATURE:

<400> SEQUENCE: 20

Leu Pro Ser Ser Ala Asp Val Glu Phe
1               5

<210> SEQ ID NO 21
<211> LENGTH: 10
<212> TYPE: PRT
<213> ORGANISM: H. sapiens
<220> FEATURE:

<400> SEQUENCE: 21

Met Glu Val Lys Pro Ile Gly His Leu Tyr
1               5                   10

<210> SEQ ID NO 22
<211> LENGTH: 8
<212> TYPE: PRT
<213> ORGANISM: H. sapiens
<220> FEATURE:

<400> SEQUENCE: 22

Tyr Arg Pro Arg Pro Arg Arg Tyr
1               5

<210> SEQ ID NO 23
<211> LENGTH: 9
<212> TYPE: PRT
<213> ORGANISM: H. sapiens
<220> FEATURE:

<400> SEQUENCE: 23

Leu Ala Met Pro Phe Ala Thr Pro Met
1               5

<210> SEQ ID NO 24
<211> LENGTH: 9
<212> TYPE: PRT
<213> ORGANISM: H. sapiens
<220> FEATURE:

<400> SEQUENCE: 24

Ala Arg Gly Pro Glu Ser Arg Leu Leu
1               5

<210> SEQ ID NO 25
<211> LENGTH: 9
<212> TYPE: PRT
<213> ORGANISM: H. sapiens
<220> FEATURE:

<400> SEQUENCE: 25

Tyr Tyr Trp Pro Arg Pro Arg Arg Tyr
1               5

<210> SEQ ID NO 26
<211> LENGTH: 9
<212> TYPE: PRT
<213> ORGANISM: H. sapiens
<220> FEATURE:

<400> SEQUENCE: 26

```
Ala Ala Arg Ala Val Phe Leu Ala Leu
  1               5
```

<210> SEQ ID NO 27
<211> LENGTH: 12
<212> TYPE: PRT
<213> ORGANISM: H. sapiens
<220> FEATURE:

<400> SEQUENCE: 27

```
Thr Gln His Phe Val Gln Glu Asn Tyr Leu Glu Tyr
  1               5                  10
```

<210> SEQ ID NO 28
<211> LENGTH: 11
<212> TYPE: PRT
<213> ORGANISM: H. sapiens
<220> FEATURE:

<400> SEQUENCE: 28

```
Ser Leu Leu Met Trp Ile Thr Gln Cys Phe Leu
  1               5                  10
```

<210> SEQ ID NO 29
<211> LENGTH: 14
<212> TYPE: PRT
<213> ORGANISM: H. sapiens
<220> FEATURE:

<400> SEQUENCE: 29

```
Ala Glu Leu Val His Phe Leu Leu Leu Lys Tyr Arg Ala Arg
  1               5                  10
```

<210> SEQ ID NO 30
<211> LENGTH: 14
<212> TYPE: PRT
<213> ORGANISM: H. sapiens
<220> FEATURE:

<400> SEQUENCE: 30

```
Leu Leu lys Tyr Arg Ala Arg Glu Pro Val Thr Lys Ala Glu
  1               5                  10
```

<210> SEQ ID NO 31
<211> LENGTH: 14
<212> TYPE: PRT
<213> ORGANISM: H. sapiens
<220> FEATURE:

<400> SEQUENCE: 31

```
Ala Glu Leu Val His Phe Leu Leu Leu Lys Tyr Arg Ala Arg
  1               5                  10
```

<210> SEQ ID NO 32
<211> LENGTH: 12
<212> TYPE: PRT
<213> ORGANISM: H. sapiens
<220> FEATURE:

<400> SEQUENCE: 32

```
Glu Tyr Val Ile Lys Val Ser Ala Arg Val Arg Phe
  1               5                  10
```

<210> SEQ ID NO 33
<211> LENGTH: 14

```
<212> TYPE: PRT
<213> ORGANISM: H. sapiens
<220> FEATURE:

<400> SEQUENCE: 33

Leu Leu Lys Tyr Arg Ala Arg Glu Pro Val Thr Lys Ala Glu
 1               5                  10

<210> SEQ ID NO 34
<211> LENGTH: 20
<212> TYPE: PRT
<213> ORGANISM: H. sapiens
<220> FEATURE:

<400> SEQUENCE: 34

Pro Gly Val Leu Leu Lys Glu Phe Thr Val Ser Gly Asn Ile Leu Thr
 1               5                  10                  15

Ile Arg Leu Thr
            20

<210> SEQ ID NO 35
<211> LENGTH: 18
<212> TYPE: PRT
<213> ORGANISM: H. sapiens
<220> FEATURE:

<400> SEQUENCE: 35

Ala Ala Asp His Arg Gln Leu Gln Leu Ser Ile Ser Ser Cys Leu Gln
 1               5                  10                  15

Gln Leu
```